United States Patent [19]

Pesa et al.

[11] 4,367,179

[45] Jan. 4, 1983

[54] HYDROCYANATION OF OLEFINIC ALKYL ESTERS

[75] Inventors: Frederick A. Pesa, Aurora; Anne M. Graham, Northfield, both of Ohio

[73] Assignee: The Standard Oil Company, Cleveland, Ohio

[21] Appl. No.: 234,124

[22] Filed: Feb. 13, 1981

Related U.S. Application Data

[63] Continuation-in-part of Ser. No. 77,696, Sep. 21, 1979, abandoned.

[51] Int. Cl.³ ............................................. C07C 120/20
[52] U.S. Cl. .............................. 260/465.4; 260/465.1; 260/465.8 R; 260/404
[58] Field of Search ............................. 260/465.4, 404

[56] References Cited

U.S. PATENT DOCUMENTS

| | | | |
|---|---|---|---|
| 2,385,741 | 9/1945 | Teter | 260/465.3 |
| 2,698,337 | 12/1954 | Heider et al. | 260/465.4 X |
| 2,904,581 | 9/1959 | Coraor et al. | 260/465.4 |
| 3,132,175 | 5/1964 | Born et al. | 260/465.4 X |
| 3,168,558 | 2/1965 | Kurhajec et al. | 260/465.4 X |
| 3,278,575 | 10/1966 | Davis et al. | 260/465.3 |
| 3,278,576 | 10/1966 | Davis | 260/465.3 |
| 3,480,660 | 11/1969 | Walker et al. | 260/465.3 |
| 3,644,467 | 2/1972 | Koberstein et al. | 260/465.4 X |
| 3,644,468 | 2/1972 | Koberstein et al. | 260/465.4 X |
| 3,925,445 | 12/1975 | King et al. | 260/465.4 X |

OTHER PUBLICATIONS

Migrdichian, The Chemistry of Organic Cyanogen Compounds; Reinhold Pub. Corp.; 1947, pp. 219–221.

Houben—Weyl, Bond VIII, Methoden der Organischem Chemie Sauerstoffverbindgungen III, 1952; pp. 266–278.

*Primary Examiner*—Joseph Paul Brust
*Attorney, Agent, or Firm*—Salvatore P. Pace; Herbert D. Knudsen; Larry W. Evans

[57] ABSTRACT

Cyanoesters are prepared by contacting an olefinic carboxylate ester, e.g. methyl acrylate, with gaseous hydrogen cyanide in the presence of a catalyst containing an element selected from the group consisting of Group IA metals and Group IIA metals.

15 Claims, No Drawings

HYDROCYANATION OF OLEFINIC ALKYL ESTERS

CROSS-REFERENCE TO RELATED APPLICATIONS

This application is a continuation-in-part of U.S. Ser. No. 77,696 filed Sept. 21, 1979, abandoned Mar. 5, 1981.

BACKGROUND OF THE INVENTION

This invention relates to a process for the vapor phase, catalytic addition of gaseous hydrogen cyanide to alkyl carboxylate esters having an olefinic carbon to carbon double bond.

There are several known methods for hydrocyanating unactivated olefins in the vapor phase. Teter, U.S. Pat. No. 2,385,741 describes the addition of hydrogen cyanide to unactivated olefins in the presence of a finely divided metallic cobalt catalyst. Davis, U.S. Pat. Nos. 3,278,575 and 3,278,576, discloses that finely divided metallic nickel or palladium can also be employed to catalyze the addition of hydrogen cyanide to unactivated olefins. The highest yield of organic nitriles obtained by any of these processes is 42%.

Houben-Weyl, Bond VIII, Methoden Der Organischem Chemie Sauerstoffverbindgungen III, 1952 at pages 266–278 describes the hydrocyanation of various olefinic compounds. Most of the reactions described are liquid phase reactions, some using alkaline catalysts such as KCN. A vapor phase reaction disclosed in Houben-Weyl utilizes an aluminum or silicon dioxide catalyst, preferably activated with a heavy metal salt such as cupric cyanide or zinc cyanide.

Coraor, U.S. Pat. No. 2,904,581 discloses that organic nitriles can be prepared from activated olefins. Activated olefins are hydrocarbons which contain an activating group in close proximity to an olefinic carbon atom. Preferably this activating group is adjacent to an olefinic carbon. Yields as high as 80% have been obtained by this process. Unfortunately, this is a liquid phase process and both hydrogen cyanide and the activated olefin tend to polymerize at the disclosed reaction conditions. Also, it is very difficult to separate the homogeneous catalyst from the reaction product.

SUMMARY OF THE INVENTION

The inventive process results in higher yields of organic nitriles than the prior art vapor phase processes. Furthermore, these higher yields are accomplished at substantially lower temperatures and because the inventive process is conducted in the vapor phase, the hydrogen cyanide and activated olefin polymerization problem is eliminated.

It has now been discovered that nitriles can be produced by contacting an activated olefin with gaseous hydrogen cyanide in the presence of a catalyst containing at least one element selected from the group consisting of Group IA and IIA of the Periodic Table. In particular, the inventive process results in high yields of cyanoesters when alkyl carboxylate esters, such as alpha, beta-unsaturated alkyl acrylates are contacted with gaseous hydrogen cyanide in the vapor phase in the presence of a catalyst containing a Group IA metal or a Group IIA metal. The process of the present invention produces unexpectedly superior results when alkyl carboxylate esters are hydrocyanated as compared to other activated olefins.

DETAILED DESCRIPTION OF THE INVENTION

According to the present invention, cyanoesters are produced by the catalytic addition of hydrogen cyanide to carboxylate esters. The overall reaction taking place in this process is represented by the following equation.

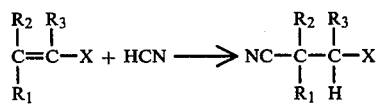

wherein $R_1$, $R_2$, $R_3$ and $X$ are defined below.

Nitriles, such as cyanoesters are well known organic chemicals having a wide variety of uses as solvents and the like. They are also important intermediates for the preparation of a broad spectrum of organic chemicals as described, for example in the text "The Chemistry of Organic Cyanogen Compounds" by V. Migridichian, American Chemical Society Monograph No. 105, Reinhold Publishing Company (New York, 1947).

Reactants

The activated olefin reactants which are employed in the process of the present invention are carboxylate esters which have one olefinic moiety, do not contain an acetylinic moiety or groups which would interfere with the hydrocyanation process, and may be represented by the general formula:

wherein $R_1$, $R_1$ and $R_3$ are each independently selected from the group consisting of:

(1) hydrogen;
(2) $C_{1-4}$ alkyl;

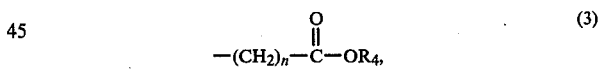

wherein $R_4$ is hydrogen or a $C_{1-4}$ alkyl and n is 0 to 4;
and

wherein $R_5$ is hydrogen or a $C_{1-4}$ alkyl and s is 0 to 4;
and wherein X is represented by the formula

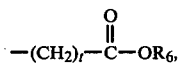

wherein $R_6$ is a $C_{1-12}$ alkyl and t is 0 to 2.

Examples of carboxylate esters suitable as reactants in the process of the present invention include but are not limited to methyl acrylate, ethyl acrylate, higher alkyl acrylates, methylmethacrylate, ethyl methacrylate, ethyl crotonate and the like. Preferably, $R_1$, $R_2$ and $R_3$ are each independently selected from:
(1) hydrogen;
(2) $C_{1-4}$ alkyl;
and X is represented by the formula:

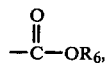

wherein $R_6$ is a $C_{1-4}$ alkyl.

The activated olefin, that is the olefinic ester, is contacted in the vapor phase with gaseous hydrogen cyanide to produce the cyanoester. The instant reaction will proceed with either excess olefinic ester or excess hydrogen cyanide. However, the use of excess olefinic esters is preferred, since this minimizes the loss of HCN. In addition, we have found that conversion to the cyanoester begins to decrease as the HCN excess increases. Accordingly, it is preferred to employ a molar ratio of olefinic ester to HCN of greater than or equal to one and preferably between about 1:1 to about 10:1.

If desired, a carrier gas which is inert to the reactants, products and catalysts can be included in the reaction system. Thus, gases such as nitrogen, the noble gases, lower alkanes, carbon monoxide, carbon dioxide, ammonia and minor amounts of hydrogen sulfide can be added to the reaction system.

Process Conditions

In carrying out the inventive process, the olefinic ester and hydrogen cyanide in the vapor phase are contacted with a catalyst as described below. This process is preferably conducted on a continuous basis but it can also be accomplished in a batch mode. Either fixed or fluid catalyst beds can be used. The reaction temperature is normally maintained between 40° C. and 350° C., preferably 150° C. to 300° C. The reaction pressure is normally maintained at 0–100 psig, preferably 10–40 psig. When the process is carried out on a continuous basis, the contact time is normally 10 seconds to 10 minutes, preferably 10 seconds to 5 minutes.

Catalysts

The heterogeneous catalyst employed in this process comprises at least one metal element selected from the group consisting of Groups IA and IIA of the Periodic Table. Preferred catalysts comprise at least one K, Li, Cs, Ca, Ba, Mg and mixtures thereof. Especially preferred catalysts contain at least one of K, Li and Cs. The catalyst may be promoted with metals such as Ru, Cr and Mn. The Group IA metal or Group IIA metal containing catalysts generally consist of any compound containing the requisite metal component which is stable at ordinary room temperature and pressure and which upon heating in air may either remain unreacted or decompose to form the corresponding metal oxide. Suitable metal compounds which upon drying and/or calcining, that is, heating in air at elevated temperatures of about 100° C. to about 600° C. yield suitable catalysts for use in the present invention include but are not limited to the Group IA metal and Group IIA metal oxides, hydroxides, inorganic salts such as ferrocyanides, nitrates, phosphates, halides, carbonates, silicates, aluminates, titanates, cyanides and salts of organic acids such as the acetates, formates and butyrates. Preferred catalysts contain oxygen or oxygen containing anions. Compounds which are somewhat basic in nature or which at least in part react with hydrogen cyanide to form metal cyanides have been found to be particularly effective. The catalyst of the present invention is preferably substantially free of nickel.

The catalyst can be prepared by methods well known in the art and may be supported or unsupported. For example, these catalysts can be produced by evaporating a solution of a soluble compound on an inert carrier, or mixing an aqueous slurry of an insoluble compound or of the free metal with an inert carrier, filtering, pressing, drying and calcining the filter cake, and finally grinding the filter cake to the desired particle size. The inert carriers which may used with this catalyst include aluminates, silicates, titanates, zirconia, phosphates and mixtures thereof. Preferred carriers are aluminates and silicates. Basic compounds such as quartz, diatomaceous earth, various clays and pumice may also be used. If no carrier is utilized, the catalyst may be formed by methods known in the art such as pelletting, tabletting and the like.

Recovery

The reaction product obtained upon completion of the reaction of the process of the present invention is partially in the gas phase. This reaction product can be subjected to suitable known separation techniques to obtain the desired end product. For example, the product can be condensed to a liquid. The liquid product can then be filtered to remove any catalyst which may have been carried over from the reactor, or which is present due to its utilization in a batch type process, and the product may then be separated into component parts by the use of solvent extraction and distillation.

SPECIFIC EMBODIMENTS OF THE INVENTION

In order to more clearly illustrate the present invention, the following working examples are presented. In these examples, the following definition is used:

$$\% \text{ of Yield} = \frac{\text{Moles of Nitrile Product Formed}}{\text{Moles of HCN Fed}} \times 100$$

When the olefinic reactant is an olefinic ester, the nitrile product is the corresponding cyanoester.

EXAMPLE 1

A catalyst containing lithium was prepared from 7.6% lithium acetate on a low surface area alumina as follows. First, 4.11 grams of lithium acetate were dissolved in 20 grams of water. Next, 50 grams of a low surface area alumina, that is alumina with a surface area of less than 20 square meters per gram, were stirred into the lithium solution. This mixture was dried for 15 hours at 125° C. and calcined for 16 hours at 350° C.

Approximately 40 cc. of the above catalyst were charged to a 40 cc. tubular stainless steel reactor. A furnace heated the reactor while nitrogen flowed over the catalyst bed. When the reactor temperature reached 250° C., the inflowing gas was changed to a mixture of about 7% to about 10% HCN in nitrogen, and the system was allowed to equilibrate for 15 minutes. Methyl acrylate was then pumped in at the rate of 10 cc. per hour. The output of the reactor was passed to a pair of dry ice cooled glass condensors, and the product was collected. The product was warmed to room temperature, weighed and analyzed by gas chromatography.

The reaction conditions and tests results are reported in Table I.

EXAMPLES 2-5

A catalyst containing potassium was prepared from a mixture of 11.2 weight percent $KNO_3$ on a low surface area alumina as follows. First, 6.31 grams of $KNO_3$ were dissolved in 20 grams of water. Next, 50 grams of a low surface area alumina, i.e. alumina with a surface area of less than 20 square meters per gram, were mixed with the aqueous potassium solution. This mixture was dried for 15 hours at 125° C. and calcined for 5 hours at 260° C. and 15 hours at 538° C. The catalyst prepared above was tested for the hydrocyanation of methyl acrylate as described in Example 1. The test results are shown in Table I.

EXAMPLES 6-8

Catalysts containing the Group IA or Group IIA metal elements cesium, calcium and barium were prepared according to the procedure described in Example 2. These catalysts were tested for the hydrocyanation of methyl acrylate as described in Example 1. The precalcined catalyst material, support material and test results for each of these examples are reported in Table I.

EXAMPLE 9

A catalyst comprising $MgAl_2O_4$ was prepared as follows. First, 85.47 grams of $Mg(NO_3)_2.6H_2O$ were dissolved in water. Next, 33.99 grams of $Al_2O_3$ powder were slurried in water. These two aqueous solutions were mixed together and evaporated to the consistency of toothpaste. The mixture was then dried for 15 hours at 125° C. and calcined 5 hours at 260° C. and 20 hours at 538° C. This catalyst was tested for the hydrocyanation of methyl acrylate as described in Example 1 and the test results are reported in Table I.

EXAMPLES 10-11

Catalysts containing potassium were prepared by the technique described in Example 9 using silica and alumina, respectively, as supports. These catalysts were tested for the hydrocyanation of methyl acrylate as described in Example 1. The catalyst/support components, reaction conditions and test results are reported in Table I.

EXAMPLE 12

A catalyst was prepared from a mixture comprising 23.78 weight percent of $KMn(CN)_6$ on a low surface area alumina as follows. First, 15.6 grams of $KMn(CN)_6$ were dissolved in 20 grams of water. 50 grams of a low surface area alumina were mixed with this aqueous solution. The mixture was then dried for 15 hours at 125° C. and calcined for 3 hours at 350° C. This catalyst was tested for the hydrocyanation of methyl acrylate as described in Example 1 and the test results are reported in Table I.

EXAMPLES 13-15

Catalysts containing potassium were prepared according to the procedure set forth in Example 12 and were tested as described in Example 1. The catalyst components, supports and test results are reported in Table I.

COMPARATIVE EXAMPLE A

Alumina alone was tested for activity in the vapor phase hydrocyanation of methyl acrylate in the experimental apparatus described in Example 1 and as reported in Table II, alumina alone was shown to be substantially inert for the reaction.

COMPARATIVE EXAMPLES B & C

Transition metal catalysts comprising copper and chromium supported on silica were prepared according to the procedure described in Example 9 and were tested for the hydrocyanation of methyl acrylate in the experimental apparatus described in Example 1. Reaction conditions and test results are reported in Table II.

COMPARATIVE EXAMPLES D & E

Transition metal catalysts comprising nickel and tin supported on silica were prepared according to the procedure of Example 9. As metallic or zero valent nickel catalysts are disclosed as catalyzing the hydrocyanation of olefins, the valence of the catalyst was reduced prior to testing for the hydrocyanation of methyl acrylate. Reaction conditions and test results are reported in Table II.

EXAMPLES 16-26

Catalysts comprising $CaAl_2O_4$ were prepared as follows. First, 78.72 grams of $Ca(NO_3)_2.4H_2O$ were dissolved in water. Also, 33.99 grams of $Al_2O_3$ powder were slurried in water. These two aqueous solutions were mixed together and evaporated to the consistency of toothpaste. The mixture was then dried for 15 hours at 125° C. and calcined for 5 hours at 260° C. and 20 hours at 538° C. The catalyst was tested for the hydrocyanation of methyl acrylate in the experimental apparatus described in Example 1 except that the process conditions were adjusted as shown in Table II. The process conditions, and results of these tests are reported in Table II.

EXAMPLES 27 & 28

A catalyst comprising $CaTiO_3$ was prepared according to the procedure of Examples 16-26, except that calcium oxide was utilized as the Group IIA metal component, and titanium dioxide powder was utilized rather than alumina. The catalyst was tested for the hydrocyanation of methyl acrylate and results are reported in Table II.

EXAMPLES 29-31

Catalysts containing lithium were prepared according to the procedure set forth in Example 1, and tested for the hydrocyanation of methyl acrylate under reaction conditions set forth in Table II. Results of the tests are reported in Table II.

EXAMPLES 32-37

Catalysts containing potassium were prepared according to the procedure set forth in Example 2 and were tested for the hydrocyanation of methyl acrylate under reaction conditions set forth in Table II. Results of the tests are reported in Table II.

COMPARATIVE EXAMPLES F, G and H

Catalysts prepared according to the procedure described in Example 2 were tested for the hydrocyanation of various "activated" olefins, particularly acrylic acid, acrolein, and acrylonitrile in the experimental apparatus described in Example 1. As reported in Table III, the percent yield of nitriles obtained in each of these examples was approximately 1%.

EXAMPLE 38

A catalyst was prepared according to the procedure described in Example 2, except that KOH was used as the potassium containing component. The molar amount of potassium present in the catalyst of Example 38 was equal to that of Examples F, G and H. This catalyst was tested for the hydrocyanation of methyl acrylate under the reaction conditions set forth in Table III.

COMPARATIVE EXAMPLES I, J and K

The liquid phase hydrocyanation of methyl acrylate was attempted in a glass flask containing 100 ml of methyl acrylate, 50 ml of dimethylsulfoxide solvent, one-half percent by weight hydroquinone polymerization inhibitor, and the following catalyst, Example I: $Ni(CO)_2(triphenylphosphine)_2$ ($2.14 \times 10^{-3}$ moles); Examples J & K: $KCN$ ($4.28 \times 10^{-3}$ moles). The liquid phase system was heated to reflux at about 85° C. while nitrogen was bubbled through the liquid. The gas stream was then switched to 8% HCN in nitrogen and the reaction allowed to proceed. In each of the liquid phase reactions, a considerable amount of polymer was formed, despite the addition of polymerization inhibitor to the reaction mixture. In addition, the reaction mixtures became deeply colored red, presumably due to HCN polymerization.

As is demonstrated by the results reported in the Examples and Tables above, the process of the present invention permits the vapor phase hydrocyanation of olefinic carboxylate esters to form cyanoesters in high yields. It is unexpectedly advantageous to utilize the process of the present invention with olefinic carboxylate ester reactants, as compared to other "activated olefins". The process of the present invention, being a vapor phase reaction, overcomes the problems inherent in the liquid phase hydrocyanation of olefins, namely the polymerization of the reactants.

Thus it should be apparent to those skilled in the art that the subject invention accomplishes the object set forth above. It is to be understood that the subject invention is not to be limited by the examples set forth herein. These have been provided merely to demonstrate operability, and the selection of Group IA and Group IIA metal containing compounds, promoter element containing compounds if any, olefinic ester feeds and reaction conditions can be determined from the total specification disclosure provided, without departing from the spirit of the invention herein disclosed and described, the scope of the invention including modifications and variations that fall within the scope of the attached claims.

TABLE I

Vapor Phase Hydrocyanation of Methyl Acrylate Using Group IA Metal and Group IIA Metal Catalysts

| Example Number | Catalyst And Support | Precalcined Catalyst Metal Component[c] | % Yield (3 Methyl Cyanoester) |
|---|---|---|---|
| 1 | Li/LSAA[a] | 7.6% LiOAc | 80.4 |
| 2 | K/LSAA | 11.2% $KNO_3$ | 98.4 |
| 3 | K/LSAA | 11.2% $KNO_3$ | 85.8 |
| 4 | K/LSAA | 11.2% $KNO_3$ | 83.8 |
| 5 | K/LSAA | 11.2% $KNO_3$ | 85.2 |
| 6 | Cs/LSAA | 19.57% $CsNO_3$ | 71.5 |
| 7 | Ca/HSAA[b] | 22.76% $Ca(NO_3)_2$ | 60.9 |
| 8 | Ba/LSAA | 24.60% $Ba(NO_3)_2$ | 64.7 |
| 9 | $MgAl_2O_4$ | $Mg(NO_3)_2$ | 43.3 |
| 10 | $K_2Si_2O_5$ | $KNO_3$ | 73.2 |
| 11 | $K_2Al_2O_4$ | $KNO_3$ | 53.8 |
| 12 | $KMnO_x$/LSAA | 23.78% $KMn(CN)_6$ | 58.1 |
| 13 | $KCrO_x$/HSAA | 10.81% $K_2CrO_4$ | 90.6 |
| 14 | $K_4RuO_x$/HSAA | 12.72% $K_4Ru(CN)_6$ | 25.5 |
| 15 | K/LSAA | 8.92% $K_2HPO_4$ | 75.6 |

[a] LSAA = Low Surface Area Alumina (approximately 5 sq. m/gm)
[b] HSAA = High Surface Area Alumina (approximately 100 sq. m/gm)
[c] Percentages are by weight based upon total catalyst component and support
- formulas do not include water of hydration
$x$ = number of oxygens needed to satisfy valence requirements of the other elements
Methyl Acrylate Feed Rate: 10cc/hr
HCN Feed Rate: 50 cc/minute (7%–10% HCN, 90%–93% $N_2$)
Temperature: 250° C.
Pressure: Atmospheric

TABLE II

Vapor Phase Hydrocyanation of Methyl Acrylate Under Various Reaction Conditions

| Example No. | Catalyst and Support | Precalcined Catalyst Metal Component | Temperature °C. | Flow Rate Methylacrylate (cc/hr.) | Flow Rate HCN (cc/min.) | % Yield (3-methylcyanoester) |
|---|---|---|---|---|---|---|
| A | $Al_2O_3$ | — | 200 | 10 | 100 | 0.5 |
| B | $CuCrO_x$/$SiO_2$ | $CuCrO_x$ | 100 | 10 | 100 | 0 |
| C | $CuCrO_x$/$SiO_2$ | $CuCrO_x$ | 200 | 10 | 100 | 0 |
| D | $NiSnO_x$/$SiO_2$ | $NiSnO_x$ | 200 | 10 | 100 | 2.2 |
| E | $NiSnO_x$/$SiO_2$ | $NiSnO_x$ | 300 | 10 | 100 | 5.1 |
| 16 | $CaAl_2O_4$ | $Ca(NO_3)_2$ | 125 | 10 | 50 | 28.7 |
| 17 | $CaAl_2O_4$ | $Ca(NO_3)_2$ | 175 | 10 | 50 | 15.2 |
| 18 | $CaAl_2O_4$ | $Ca(NO_3)_2$ | 200 | 10 | 50 | 27.1 |
| 19 | $CaAl_2O_4$ | $Ca(NO_3)_2$ | 225 | 10 | 50 | 46.7 |
| 20 | $CaAl_2O_4$ | $Ca(NO_3)_2$ | 250 | 10 | 50 | 74.8 |
| 21 | $CaAl_2O_4$ | $Ca(NO_3)_2$ | 275 | 10 | 50 | 54.6 |
| 22 | $CaAl_2O_4$ | $Ca(NO_3)_2$ | 175 | 10 | 100 | 24.9 |
| 23 | $CaAl_2O_4$ | $Ca(NO_3)_2$ | 200 | 10 | 100 | 13.5 |
| 24 | $CaAl_2O_4$ | $Ca(NO_3)_2$ | 200 | 10 | 100 | 58.6 |
| 25 | $CaAl_2O_4$ | $Ca(NO_3)_2$ | 200 | 10 | 100 | 59.5 |
| 26 | $CaAl_2O_4$ | $Ca(NO_3)_2$ | 225 | 10 | 100 | 55.1 |
| 27 | $CaTiO_3$ | CaO | 175 | 10 | 50 | 64.3 |
| 28 | $CaTiO_3$ | CaO | 200 | 10 | 100 | 34.3 |
| 29 | Li/LSAA[b] | 7.6% LiOAc | 250 | 10 | 50 | 88.8 |
| 30 | Li/LSAA | 7.6% LiOAc | 250 | 10 | 25 | 81.6 |
| 31 | Li/LSAA | 7.6% LiOAc | 250 | 2 | 50 | 67.3 |
| 32 | K/LSAA | 11.2% $KNO_3$ | 250 | 10 | 50 | 79.5 |
| 33 | K/LSAA | 11.2% $KNO_3$ | 250 | 2.1 | 50 | 49.2 |
| 34 | K/LSAA | 11.2% $KNO_3$ | 275 | 2 | 50 | 54.7 |
| 35 | K/LSAA | 11.2% $KNO_3$ | 250 | 10 | 50 | 79.2 |

TABLE II-continued

Vapor Phase Hydrocyanation of Methyl Acrylate Under Various Reaction Conditions

| Example No. | Catalyst and Support | Precalcined Catalyst Metal Component | Temperature °C. | Flow Rate Methylacrylate (cc/hr.) | HCN (cc/min.) | % Yield (3-methylcyanoester) |
|---|---|---|---|---|---|---|
| 36 | K/LSAA | 11.2% KNO₃ | 250 | 20 | 100 | 70.6 |
| 37 | K/LSAA | 11.2% KNO₃ | 300 | 30 | 150 | 69.6 |

$^a$Percentages are by weight based upon total catalyst component and support.
Formulas do not include water of hydration
$^b$LSAA = Low surface area Alumina (approximately 5 sq. m/gm)
HCN Feed: 7% to 10% HCN, 90% to 93% N$_2$
Pressure: Atmospheric

TABLE III

Hydrocyanation of Activated Olefins Using Potassium Catalysts Supported on High Surface Area Alumina

| Example No. | Precalcined Catalyst Metal Component | Activated Olefin | Temperature °C. | Flow Rate Olefin (cc/hr) | HCN (cc/min) | % Yield of Nitrile |
|---|---|---|---|---|---|---|
| F | KNO₃ | Acrylic Acid | 150 | 10 | 50 | 1 |
| G | KNO₃ | Acrolein | 150 | 10 | 50 | 1 |
| H | KNO₃ | Acrylonitrile | 150 | 10 | 50 | 1 |
| 38 | KOH | Methylacrylate | 100 | 10 | 100 | 17.7 |

HCN Feed: 7-10% HCN, 90-93% N$_2$
Pressure: Atmospheric

We claim:

1. A process for producing cyanoester comprising contacting an olefinic, alkyl carboxylate ester in the vapor phase with gaseous hydrogen cyanide in the presence of a catalyst containing at least one element selected from the group consisting of Li, Na, K, Rb, Cs, Be, Mg, Ca and Sr, wherein said catalyst is prepared by calcining in air, at a temperature of about 100° C. to about 600° C., a compound containing said element, said compound being stable at room temperature and atmospheric pressure, and wherein said reactant ester is represented by the formula:

$$\begin{array}{c} R_2 \ R_3 \\ | \ \ | \\ C=C-X \\ | \\ R_1 \end{array}$$

wherein R$_1$, R$_2$ and R$_3$ are each independently selected from:
(1) hydrogen;
(2) C$_{1-4}$ alkyl;

$$-(CH_2)_n-\overset{\overset{\displaystyle O}{\|}}{C}-OR_4, \quad (3)$$

wherein R$_4$ is hydrogen or a C$_{1-4}$ alkyl and n is 0 to 4; and $$-(CH_2)_s-\overset{\overset{\displaystyle O}{\|}}{C}-R_5, \quad (4)$$

wherein R$_5$ is hydrogen or a C$_{1-4}$ alkyl and s is 0 to 4;
and wherein X is represented by the formula $$-(CH_2)_t-\overset{\overset{\displaystyle O}{\|}}{C}-OR_6,$$

wherein R$_6$ is a C$_{1-12}$ alkyl and t is 0 to 2.

2. The process of claim 1 wherein R$_1$, R$_2$ and R$_3$ are each independently selected from H and C$_{1-4}$ alkyl.

3. The process of claim 1 wherein R$_1$, R$_2$ and R$_3$ are each independently selected from H and CH$_3$.

4. The process of claim 1, wherein X is selected from the group consisting of $$-\overset{\overset{\displaystyle O}{\|}}{C}-OR_6$$

wherein R$_6$ is a C$_{1-4}$ alkyl.

5. The process of claim 1, wherein said ester is methyl acrylate.

6. The process of claim 1 wherein the molar ratio of ester to HCN is about 1:1 to about 10:1.

7. The process of claim 1 wherein the reaction pressure is about 0 psig to about 100 psig.

8. The process of claim 1 wherein the reaction temperature is about 100° C. to about 300° C.

9. The process of claim 1 wherein the catalyst comprises at least one of Li, Na, K, Rb, Cs, Mg, Ca, Sr, Ba and mixtures thereof.

10. The process of claim 1, wherein the catalyst comprises at least one of Li, K, Cs, Ca, Ba, Mg and mixtures thereof.

11. The process of claim 1, wherein the catalyst additionally comprises a promoter selected from Ru, Cr, Mn and Cu.

12. The process of claim 1, wherein the catalyst is substantially free of nickel.

13. The process of claim 1, wherein said compound is selected from said elements in the form of oxides, hydroxides, cyanides, ferrocyanides, nitrates, phosphates, halides, carbonates, silicates, aluminates, titanates, acetates, formates and butyrates.

14. The process of claim 1, wherein the catalyst is supported on a substantially inert carrier.

15. The process of claim 14, wherein the carrier is selected from alumina, silica, alumina-silica, titania and zirconia.

* * * * *